(12) United States Patent
Feldman et al.

(10) Patent No.: US 8,911,380 B1
(45) Date of Patent: Dec. 16, 2014

(54) RESPIRATION MONITORING SYSTEM AND METHOD

(75) Inventors: Doron Feldman, Williamsville, NY (US); Jerrold Lerman, Buffalo, NY (US); Ronen Feldman, Ellicott City, MD (US); John Moser, Dover, DE (US); Uri Feldman, Columbia, MD (US)

(73) Assignee: Linshom, L.P., Williamsville, NY (US)

( * ) Notice: Subject to any disclaimer, the term of this patent is extended or adjusted under 35 U.S.C. 154(b) by 399 days.

(21) Appl. No.: 13/553,070

(22) Filed: Jul. 19, 2012

Related U.S. Application Data

(63) Continuation-in-part of application No. 12/759,788, filed on Apr. 14, 2010, now Pat. No. 8,579,829.

(60) Provisional application No. 61/170,594, filed on Apr. 17, 2009.

(51) Int. Cl.
*A61B 5/08* (2006.01)
*A61B 5/087* (2006.01)

(52) U.S. Cl.
CPC .............. *A61B 5/0878* (2013.01); *A61B 5/087* (2013.01)
USPC ...... 600/536; 600/538; 73/204.16; 73/204.17

(58) Field of Classification Search
CPC ... A61B 5/0803; A61B 5/0878; A61B 5/4818
USPC ................................................. 600/529–543
See application file for complete search history.

(56) References Cited

U.S. PATENT DOCUMENTS

| | | | |
|---|---|---|---|
| 3,232,288 A | 2/1966 | Krobath | |
| 3,513,832 A | 5/1970 | Klemm et al. | |
| 3,903,876 A | 9/1975 | Harris | |
| 3,999,537 A | 12/1976 | Noiles | |
| 4,420,001 A | 12/1983 | Hearne | |
| 4,646,750 A | 3/1987 | Williams | |
| 5,069,222 A | 12/1991 | McDonald, Jr. | |
| 5,081,866 A * | 1/1992 | Ochiai et al. ............... | 73/204.21 |
| 5,161,541 A | 11/1992 | Bowman et al. | |
| 5,190,048 A | 3/1993 | Wilkinson | |
| 5,197,294 A | 3/1993 | Galvan et al. | |
| 5,311,875 A | 5/1994 | Stasz | |
| 5,355,893 A * | 10/1994 | Mick et al. .................... | 600/532 |

(Continued)

OTHER PUBLICATIONS

"Electrodes, Monitors, Sensors"; Sleep Review, The Journal for Sleep Specialists; Currently available at http://archive.sleepreviewmag.com/issues/articles/2008-12_03d.asp; 5 pages.

(Continued)

*Primary Examiner* — Navin Natnithithadha
*Assistant Examiner* — Eric Messersmith
(74) *Attorney, Agent, or Firm* — Rosenberg, Klein & Lee

(57) ABSTRACT

A respiration monitoring system includes a thermoelectric generator that may be mounted within a mask enclosure or free-standing, covering all or part of the nose and/or mouth of a subject. A first temperature sensor is attached to the thermoelectric generator for measuring the subject's breath. A power controller develops a difference between a preset temperature and the subject's breath temperature that is then inserted into a feedback error signal and then into a power controller which regulates the power to the thermoelectric generator to maintain a preset temperature.

30 Claims, 4 Drawing Sheets

(56) References Cited

U.S. PATENT DOCUMENTS

| | | | |
|---|---|---|---|
| 5,357,975 A | 10/1994 | Kraemer et al. | |
| 5,385,020 A | 1/1995 | Gwilliam et al. | |
| 5,800,360 A | 9/1998 | Kisner et al. | |
| 5,832,592 A | 11/1998 | Bowman et al. | |
| RE36,242 E | 6/1999 | Apisdorf | |
| 5,964,712 A | 10/1999 | Kubo et al. | |
| 6,085,576 A | 7/2000 | Sunshine et al. | |
| 6,155,986 A | 12/2000 | Brydon et al. | |
| 6,158,434 A | 12/2000 | Lugtigheid et al. | |
| 6,165,133 A | 12/2000 | Rapoport et al. | |
| 6,234,006 B1 | 5/2001 | Sunshine et al. | |
| 6,254,545 B1 | 7/2001 | Stasz et al. | |
| 6,272,933 B1 | 8/2001 | Gradon et al. | |
| 6,368,287 B1 * | 4/2002 | Hadas | 600/529 |
| 6,418,783 B2 | 7/2002 | Sunshine et al. | |
| 6,523,538 B1 | 2/2003 | Wikefeldt | |
| 6,555,821 B1 | 4/2003 | Himberg et al. | |
| 6,658,915 B2 | 12/2003 | Sunshine et al. | |
| 6,669,649 B2 | 12/2003 | Kahn | |
| 6,837,095 B2 | 1/2005 | Nakayama et al. | |
| 6,840,955 B2 | 1/2005 | Ein | |
| 6,883,364 B2 | 4/2005 | Sunshine et al. | |
| 6,954,944 B2 | 10/2005 | Feher | |
| 7,003,418 B2 * | 2/2006 | Bonne et al. | 702/100 |
| 7,028,687 B1 | 4/2006 | Silver et al. | |
| 7,089,780 B2 | 8/2006 | Sunshine et al. | |
| 7,101,341 B2 | 9/2006 | Tsukashima et al. | |
| 7,297,120 B2 | 11/2007 | Tsukashima et al. | |
| 7,354,195 B2 | 4/2008 | Sakano | |
| 7,415,126 B2 | 8/2008 | Breed et al. | |
| 7,418,981 B2 | 9/2008 | Baker et al. | |
| 7,438,072 B2 | 10/2008 | Izuchukwu | |
| 7,483,805 B2 | 1/2009 | Sparks et al. | |
| 7,525,663 B2 | 4/2009 | Kwok et al. | |
| 7,914,460 B2 | 3/2011 | Melker et al. | |
| 7,919,754 B2 | 4/2011 | Hök et al. | |
| 8,579,829 B2 * | 11/2013 | Feldman et al. | 600/537 |
| 2001/0037071 A1 | 11/2001 | Lingo, Jr. et al. | |
| 2003/0199804 A1 | 10/2003 | Ahlmen et al. | |
| 2003/0208133 A1 | 11/2003 | Mault | |
| 2004/0082872 A1 | 4/2004 | von Bahr et al. | |
| 2004/0186389 A1 | 9/2004 | Mault et al. | |
| 2005/0131504 A1 | 6/2005 | Kim | |
| 2007/0068811 A1 | 3/2007 | Tsukashima et al. | |
| 2007/0088334 A1 | 4/2007 | Hillis et al. | |
| 2007/0167855 A1 | 7/2007 | Shin et al. | |
| 2008/0078382 A1 | 4/2008 | LeMahieu et al. | |
| 2008/0082018 A1 | 4/2008 | Sackner et al. | |
| 2008/0183094 A1 | 7/2008 | Schonfuss et al. | |
| 2008/0243056 A1 | 10/2008 | Hillis et al. | |
| 2008/0281220 A1 | 11/2008 | Sharifpour | |
| 2009/0038615 A1 | 2/2009 | Bradley | |
| 2009/0078120 A1 | 3/2009 | Kummer et al. | |
| 2009/0241947 A1 * | 10/2009 | Bedini et al. | 128/203.14 |
| 2010/0007889 A1 | 1/2010 | Van Kesteren | |
| 2010/0090650 A1 | 4/2010 | Yazami et al. | |
| 2010/0175556 A1 | 7/2010 | Kummer et al. | |
| 2010/0305465 A1 * | 12/2010 | Ricks et al. | 600/538 |
| 2013/0165810 A1 * | 6/2013 | Saatchi et al. | 600/537 |

OTHER PUBLICATIONS

Shochat, et al.; "The SleepStrip TM: An apnoea screener for the early detection of sleep apnoea syndrome"; European Respiratory Journal, Jan. 1, 2002; vol. 19, No. 1; pp. 121-126.

Anesthesia Breath Detection Products; Originally available at http://salterlabs.com/ on Dec. 22, 2010. Now available at "http://web.archive.org/web/20101222181915/http://salterlabs.com/".

ThermiSense®; Oral/Nasal Thermal Airflow Sensing System; Originally available at http:/salterlabs.com/ on Dec. 13, 2010. Now available at "http://web.archive.org/web/20101213073810/http://www.salterlabs.com/index.cfm? fuseaction=products.product&product_id=15&category_id&24".

Salter-Style® 1600HF High Flow Cannula; Originally available at http:/salterlabs.com/ on Jan. 11, 2011. Now available at "http://web.archive.org/web/20110111023615/http://www.salterlabs.com/index.cfm?fuseaction=products.product&product_id=27&category_id&16".

Salter-Style® TLCannula TM, Originally available at http:/salterlabs.com/ on Jan. 3, 2011. Now available at "http://web.archive.org/web/20110103111101/http://www.salterlabs.com/index.cfm?fuseaction=products.product&product_id=26&category_id&16".

* cited by examiner

RESPIRATION MONITORING SYSTEM AND METHOD

CROSS-REFERENCES TO RELATED APPLICATIONS

This application is a Continuation-in-Part of Ser. No. 12/759,788, filed at the U.S. Patent and Trademark Office on 14 Apr. 2010, which is based upon Provisional Application Ser. No. 61/170,594, filed on 17 Apr. 2009.

FIELD OF THE INVENTION

This invention relates to systems and methods associated with monitoring the respiration of a subject or patient. In particular, this invention relates to a respiration monitoring system and method for monitoring the respiration of a subject and providing displays and alarms when respiration parameters of the subject deviate from predetermined thresholds.

Further, this invention relates to a respiration monitoring system and method that provides for the measurement of a subject's breathing parameters substantially independent of the influence of conditions within the external environment.

Still further, this invention pertains to a respiration monitoring system and method that is adaptable to measure respiration parameters within or external to an enclosed area mounted over the nose and/or mouth of a patient in the nature of a mask.

This invention relates to a respiration monitoring system and method based upon the concept of maintaining a preset temperature of a thermoelectric generator or cooler within or external a mask chamber that is independent of external environment temperatures.

This invention pertains to a respiration monitoring system and method to provide a substantially portable monitoring system that is particularly adaptable for use on-site where a patient's trauma may have occurred and prior to having the patient brought to a hospital setting (as in a field trauma, ambulance or battleground), in procedures performed in medical or dental offices and under extreme conditions (in a mine, underwater, in a fire) where it is not possible to maintain verbal contact with the subject in difficulty.

This invention relates to a respiration monitoring system and method which includes a thermoelectric generator mounted within or external a mask enclosure and which is coupled to a feedback error signal processor and compensating power controller in a feedback loop for driving the thermoelectric generator to a preset temperature.

BACKGROUND OF THE INVENTION

Brain damage and/or death of a subject are direct consequences of prolonged apnea (absence of respiration), particularly when combined with hypoxia. Diagnosing apnea and hypoventilation (a reduction in breathing rate) are of particular concern when a patient is sedated, or when their breathing fails during sleep (as in obstructive sleep apnea).

Identifying hypoventilation before apnea occurs by monitoring breathing frequency and/or breath volume of the patient allows time to intervene to stimulate breathing, relieve airway obstruction, and restore effective respiration of the subject before hypoxia occurs. Hypoxic-ischemic brain damage may result from inadequate or loss of respiration, which if not reversed early in the development, may lead to brain damage and possible death. There are numerous human tragedies of such consequences from a failure to adequately monitor respiration.

Generally, respiratory rate can be monitored continuously and non-invasively by measuring the carbon dioxide partial pressure in the exhaled breath. However, carbon dioxide measurements do not change directly with breath volume, only rate. No portable, disposable and inexpensive carbon dioxide detectors are known in the prior art.

Ventilation may also be measured by examining displacement of the chest and rib cage using sophisticated monitors found in operating rooms and in sleep laboratories. However, such monitors are non-transportable, non-portable, cumbersome to use, generally expensive and are not widely available.

At the present time, it is not believed that there are any devices that provide for non-invasive/portable/measures of ventilation in patients whose airways are not instrumented in some way.

Such a monitoring system is needed to detect the presence of breathing, to measure respiratory rate and to estimate the breathing volume in both patients in hospitals and others outside hospitals, in doctors' offices and in the community (firemen, miners and armed forces).

In addition, the limits of performance of such a respiratory monitor must address its application in trauma which may occur outside healthcare institutions, in deserts, fires and mines. Hence the device must be effective when applied internal or external to an enclosure or mask over the patient's face, and when increased or decreased ambient temperatures are present. Such temperature changes in the local environment could limit the performance of the monitor for which there must be compensation. Thus, a system is needed that provides for consistent and reliable monitoring of respiration that is independent of the ambient temperature.

PRIOR ART

In some prior art patient respiration monitoring systems, such as that provided in U.S. Pat. No. 5,069,222, respiration monitoring includes the use of thermistors to develop an electrical signal representative of a patient's breath temperature. However, such prior art systems do not take into account the effects of the ambient environmental temperature effects on the electrical signal being developed and may lead to erroneous monitoring status when the ambient temperature is similar to the breath temperature or where the ambient temperature is experiencing rapid changes in temperature.

Other prior art systems for monitoring a patient's respiration as exemplified by U.S. Pat. No. 5,190,048 provides for thermistors to be aligned with the nasal passages of a patient and mounted in an airflow sensor assembly. However, such prior art systems rely solely on the signal from the thermistors to monitor the patient's breath temperature. Such prior art systems do not provide for a feedback loop to drive a thermoelectric generator to a preset temperature to essentially isolate the monitoring system from external changing parameters.

Other prior art systems as recited in U.S. Pat. No. 6,165,133 provide for thermistors to be either inserted or positioned in the vicinity of a patient's nasal passages. Such systems are devoid of any mechanisms for solving the problem of changing ambient thermal parameters.

Other prior art respiration monitoring systems as recited in U.S. Pat. No. 6,272,933 utilize thermistor technology in the mounting system. However, such prior art systems do not address, nor describe systems and methods directed to the problem of rapidly changing environmental parameters nor the problem of obtaining a reliable respiration signal when the ambient environment temperature is close to the breath temperature of the patient.

SUMMARY OF THE INVENTION

This invention is directed to a respiration monitoring system for monitoring the respiration of a patient. The sensor may be located within a facemask, nose mask or simply adjacent to the nostrils of the subject. A first temperature sensor is located within the sensor and the first temperature sensor is coupled to a thermoelectric generator. The thermoelectric generator generates a first voltage signal representative of the patient's respiration temperature, dependent upon a preset temperature and a patient's respiration temperature during predetermined cycles of the patient's respiration. The thermoelectric generator is driven to the preset temperature during predetermined cycles of the patient's breathing. A feedback error signal processor is connected to the thermoelectric generator through a compensating power controller where the feedback error signal processor develops a processed electrical signal responsive to the difference in the patient measured breath and the preset temperature.

The feedback error signal processor operates upon the difference between the preset temperature and the temperature of the patient's breath for providing a signal to the compensating power controller that then inserts a predetermined voltage to the thermoelectric generator to drive the thermoelectric generator to a preset temperature.

An object of the subject invention is to provide a respiration monitoring system to monitor the respiration of a subject within a chamber formed by a mask covering the subject's mouth, nose and/or face or without a chamber adjacent to the mouth or nose.

A further object of the subject invention is to provide a feedback loop from a thermoelectric generator to drive the thermoelectric generator to a preset temperature during the monitoring of the patient's respiration during predetermined cycles of the subject's breathing.

A further object of the subject system is to provide a respiration monitoring system that operates substantially independent of varying external environment temperatures in order to provide an accurate monitoring of the subject's respiration.

A still further object of the subject invention is to provide a respiration monitoring system that includes a temperature controller processor for obtaining an ambient condition temperature and calculating a preset temperature followed by an operation on the preset temperature and the breath temperature of the subject to transmit a signal responsive to the differences.

A further object of the invention is to provide a respiration monitoring system and method that operates on a temperature difference between the subject's breath and a preset temperature to provide a shaped and smoothed signal inserted into a power controller for controlling a signal to a thermoelectric generator, to maintain the thermoelectric generator at the preset temperature during the overall monitoring period.

A still further object of the invention is to provide a respiration system that includes a feedback loop including a thermoelectric generator, a temperature controller processor, and a power controller to drive the temperature of the thermoelectric generator to a preset temperature substantially independent of external parameters.

DESCRIPTION OF THE PREFERRED EMBODIMENTS

Figure 1:
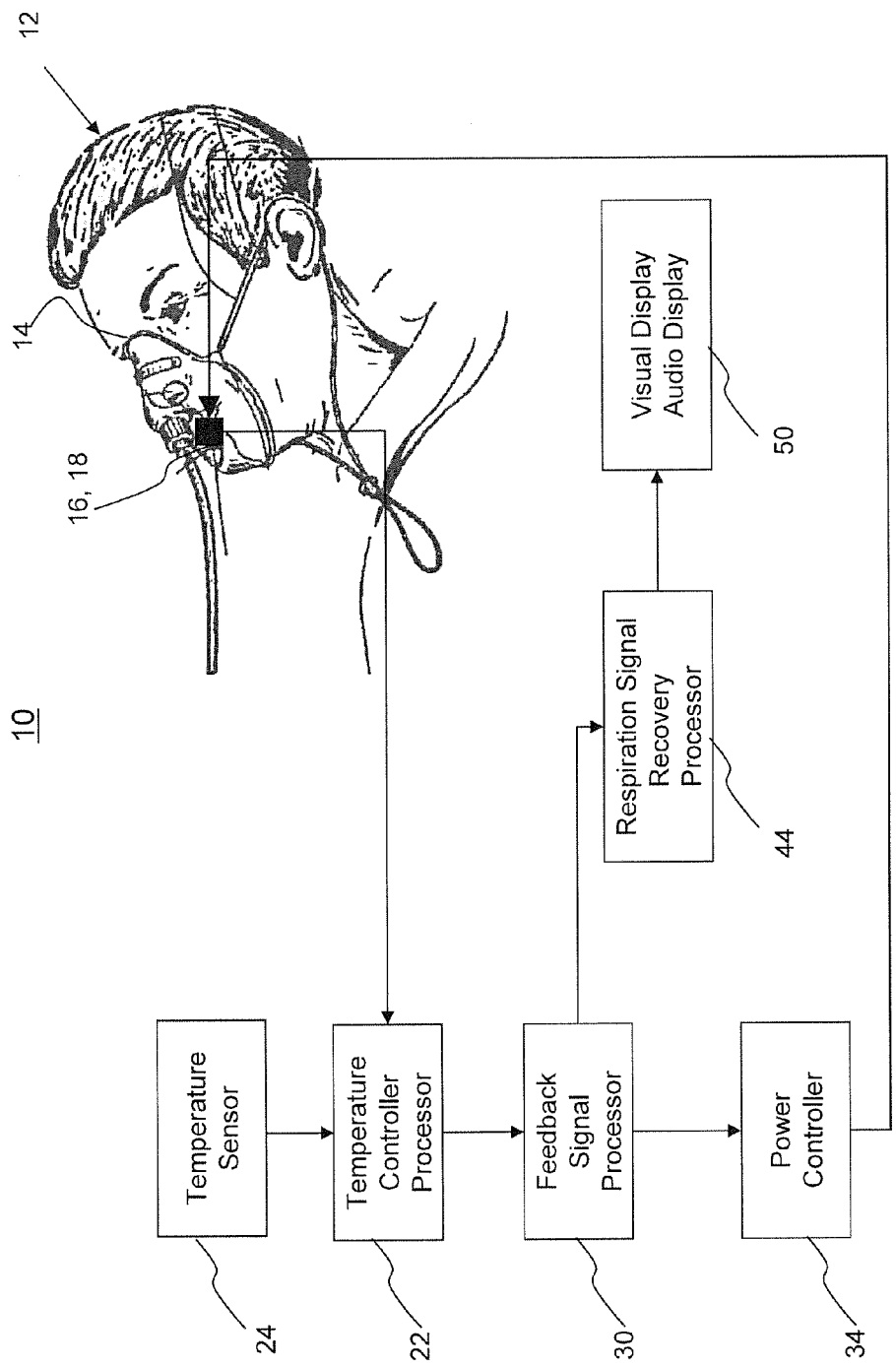
FIG. 1 is an overall perspective view, partially in block formation, showing a subject with a facemask and the associated elements of the system.

Referring now to FIGS. 1-4, there is shown respiration monitoring system 10 for monitoring the respiration of a subject 12 where the respiration is monitored within an enclosure 14. The enclosure 14 may be a mask-like device 14 that essentially covers the nose and mouth of the patient 12. The mask device or enclosure 14 is fastened to the patient 12 by flexible straps or some other fastening not important to the invention as herein described, with the exception that mask 14 be adapted to be held tightly against the skin of the patient 12 to ensure that most of the subject's breathing passes through enclosure 14. Alternatively, a temperature sensor 18, to be further described, may be mounted adjacent the nasal openings of subject 12.

Respiration monitoring system 10 is a highly portable system that may be used in operating rooms, but is especially adapted for use at external sites that do not have the full capabilities and instrumentation of a hospital operating room for monitoring the respiration of subject 12. Such systems may be used in differing environments encountered by medical personnel where system 10 can be easily transported from one area to another in a short amount of time with minimal effort, or outside healthcare systems such as by in ambulances, and worn by firemen and miners.

Of particular importance is that respiration monitoring system 10 is adapted to be used in varying external ambient conditions which may provide for ambient external temperatures covering a wide temperature range and possibly subject to rapid ambient temperature changes.

In overall concept, respiration monitoring system 10 is directed to a respiration system. which provides for monitoring substantially independent of the external ambient temperatures and determines breathing parameters during a subjects breathing cycles that are highly accurate in determining the status of subject 12.

Figure 2:
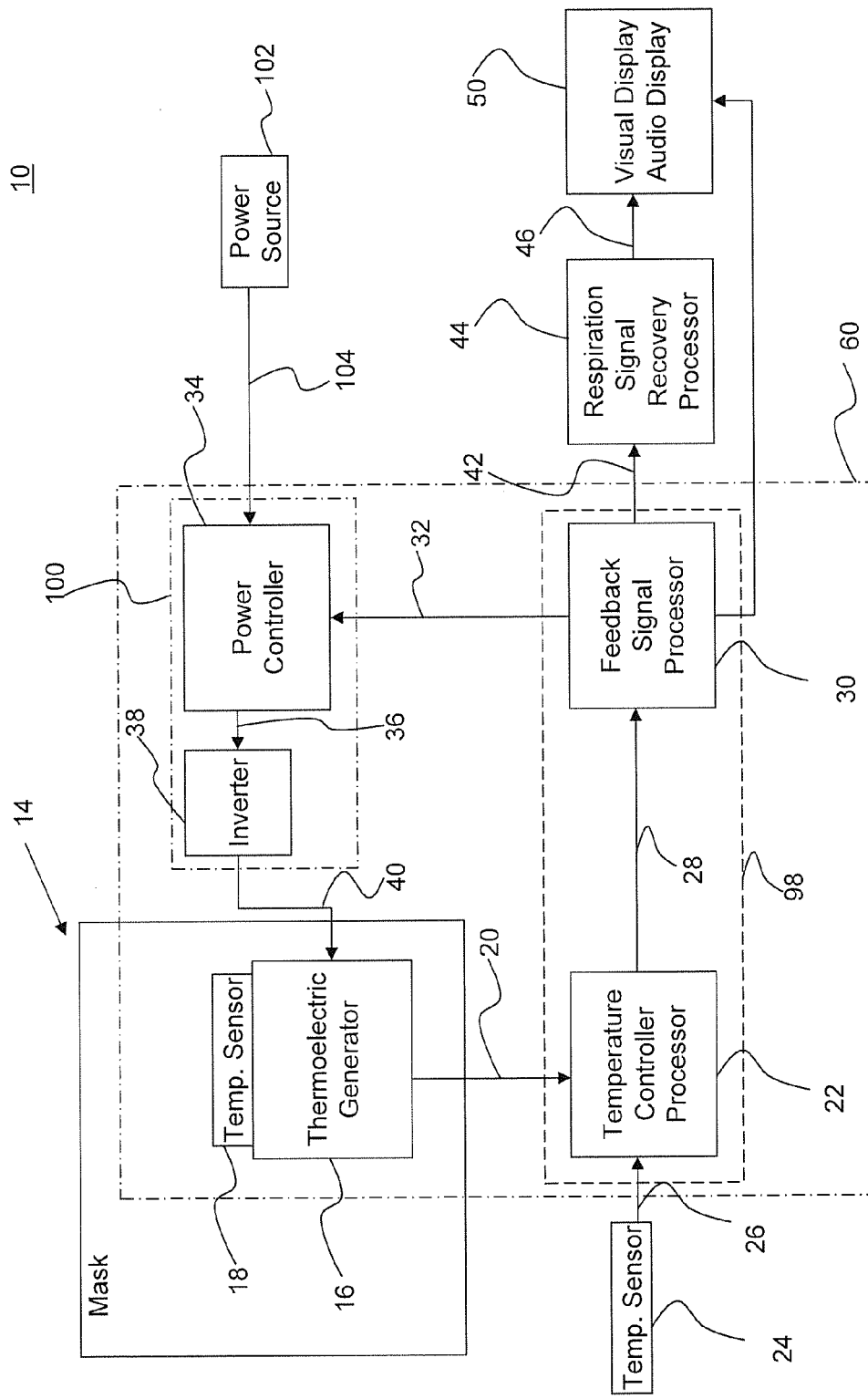
FIG. 2 is a block diagram of the respiration monitoring system for showing the components of the monitoring system.
Figure 3:
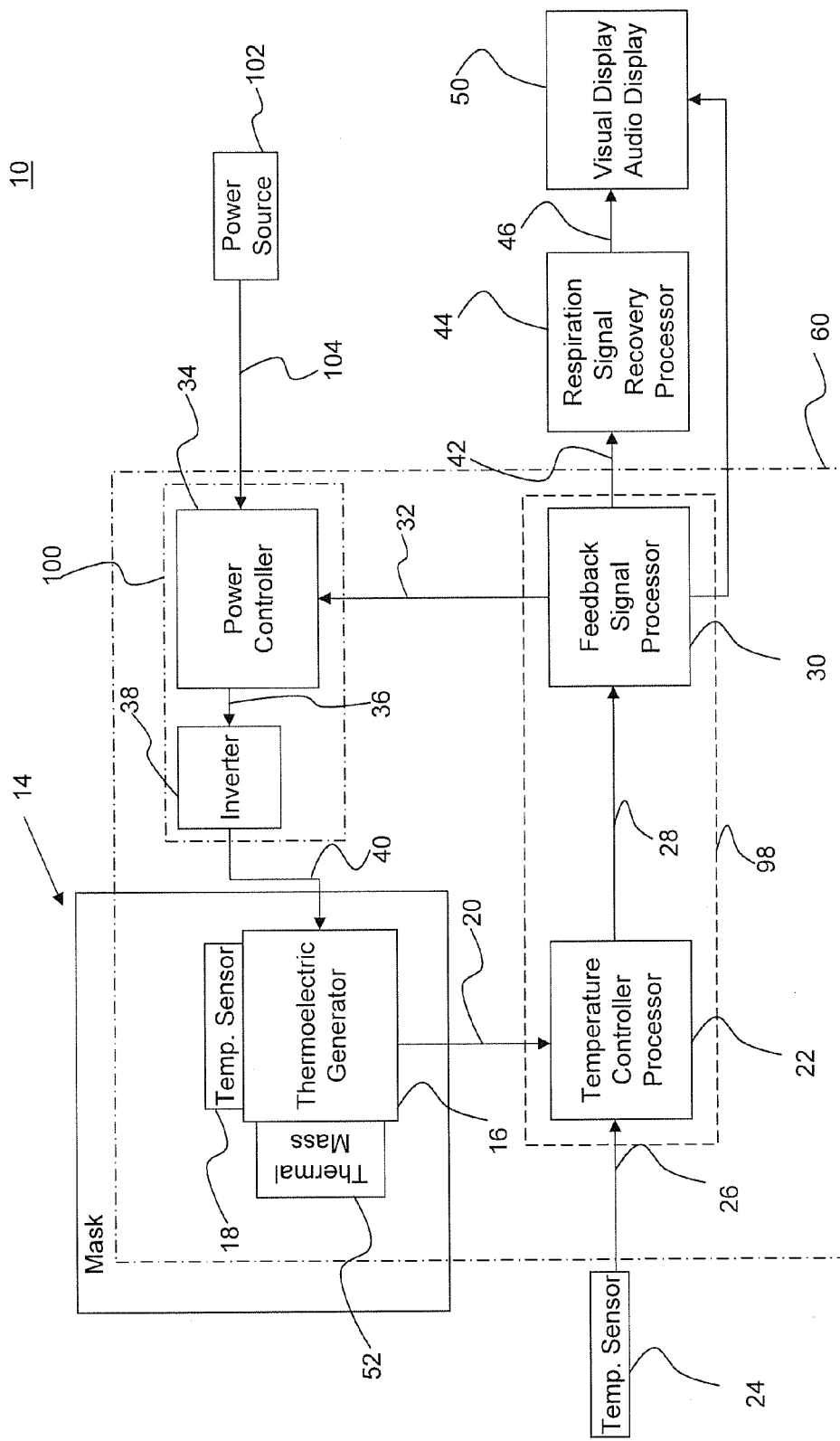
FIG. 3 is a block diagram of the respiration monitoring system showing a thermal mass attached in cooperation to a thermoelectric generator; and, FIG. 4 is a block diagram of the method for monitoring the respiration of a subject showing the feedback loop steps associated with the respiration monitoring systems.

Respiration monitoring system 10 is configured as a feedback loop represented within feedback loop block 60 shown in FIGS. 2 and 3, which minimizes the possible effects of external ambient temperature conditions in the respiration monitoring process. In order to overcome the problem of varying ambient conditions, monitoring system 10 is formed as a feedback loop from mask 14 to feedback error signal processor 98, which includes temperature controller processor 22 where the overall parameter signals are then fed back into other operating mechanisms within mask 14.

In an embodiment where no mask 14 is used, temperature sensor 18 is coupled directly to thermoelectric generator 16 whereupon a feedback loop is provided for monitoring system 10 to provide a signal to feedback error signal processor 98 and compensating power controller 100 which in turn is electrically connected to thermoelectric generator 16.

In overall concept, a temperature set point or preset temperature ($T_{sp}$) is calculated and determined based upon the external ambient temperature and the temperature sensed by the exhalation of subject 12 within the mask. 14 or temperature sensor 18. Operations are conducted on the difference between the temperature measured within mask 14 or by the temperature sensed by temperature sensor 18 and a function of the temperature of the external environment. If the temperature of the external environment is relatively close to the temperature of the respiration of patient 12, then the difference signal determined between the temperature measured within enclosure or mask 14 or the area sensed by temperature sensor 18 and the ambient temperature will be small and possibly shrouded by noise or other extraneous factors within the calculating process creating a low signal to noise ratio.

Thus, a temperature set point or preset temperature is calculated as a function of the ambient external temperature and the previous breath or respiration cycle of subject 12 and the temperature set point is set based upon either a function of the previous calculations or from a lookup table where the temperature set point can be calculated. The manner in which the set point is taken and measured may be through any number of calculations, functions or lookup tables and only important to the invention concept herein described, in that the difference between the calculation of the temperature set point is a value where the temperature set point in a particular breathing cycle minus the temperature sensed within the enclosure 14 or by the temperature sensor 18 provides a resulting signal which is easily read and is substantially free of noise considerations.

Referring now to FIGS. 1-4, there is shown an embodiment of respiration monitoring system 10 where enclosure or mask 14 is operatively coupled to subject 12 and encloses the respiratory areas of subjects 12 including both the mouth and/or nose of the patient 12. During a monitoring procedure, the breath of subject 12 is monitored for the cycles of inhalation and exhalation.

Thermoelectric generator 16 is positioned within a chamber formed by enclosure or mask 14 for generating a signal based upon the temperature differential of semiconductors comprising thermoelectric generator 16. Thermoelectric generator 16 is positioned within enclosure 14 in a manner whereby the breath of the subject directly impinges on first temperature sensor 18 attached to the thermoelectric generator 16.

Thermoelectric generator 16 uses the Peltier effect for creating a heat flux between the junction of two differing types of materials. Essentially, this is a solid-state active heat pump that transfers heat from one side of the device to the other with consumption of electrical energy depending on the direction of the current. Such a Peltier device is a heat pump and when direct current runs through it, heat is transferred from one side to the other. Thus, such a device may be used for heating/cooling and in this instance is used as a heat transport mechanism that either heats or cools. Voltage applied across thermoelectric generator 16 provides a difference in temperature that builds up between opposing sides. Thermoelectric generator 16 may be formed in many contours for differing applications and in the present system described is sized to be mounted within mask 14. Thermoelectric generator 16 may be one of many off-the-shelf commercially available systems that in the subject system 10 is particularly sized to be adaptable for insertion into the chamber of the mask or enclosure 14 or alternatively to be located adjacent the nasal passages of subject 12.

As an example, thermoelectric generator or thermoelectric cooler 16 may be a single stage thermoelectric cooler and may be commercially obtained from TEC Microsystems GmBH and in particular, may have a Model Number DX5100 OEM1, Serial #0171-0172, which has been used in fabrication of respiration monitoring system 10.

Thermistor or first temperature sensor 18 is mounted directly to thermoelectric generator or thermoelectric cooler 16 through use of some type of standard thermal epoxy or by other thermally conductive means known to those skilled in the art. The thermistor or first temperature sensor 18 may be in direct contact with thermoelectric generator 16 to produce a first voltage signal or patient respiration electrical signal responsive to the change in temperature across thermoelectric generator 16 with subject respiration electrical signal being transmitted to feedback error signal processor 98 on first signal line 20. Feedback error signal processor 98 includes temperature controller processor 22 and feedback signal processor 30 to be described in following paragraphs.

Second thermistor or second temperature sensor 24 for providing a second voltage signal on second voltage signal line 26 is mounted external to enclosure or mask 14 or sufficiently remote from subject 12 to provide an accurate representation of the ambient external temperature. Both first and second voltage signals are inserted into temperature controller processor 22 of feedback error signal processor 98, as is seen in FIGS. 1-3. However, as has previously been indicated, the ambient temperature measured by second temperature sensor 24 may be relatively close to the temperature measured by first temperature sensor 18 within mask 14 or near the breathing site of subject 12. The following paragraphs detail the operation within feedback error signal processor 98 and temperature controller processor 22 for obtaining a difference signal between the signal coming in on first signal line 20 and the signal coming in on second signal line 26 relative to the respective temperatures measured by first temperature sensor 18 and second temperature sensor 24.

As has been stated it has been found that the temperature measured by second temperature sensor 24 and the temperature measured by first temperature sensor 18 may be relatively close to each other or the ambient temperature may change rapidly. This would have an effect on taking the difference between the signals coming in on line 20 and line 26, since the change in voltage signal would be rather small and may be clouded by any noise or any other undesired random disturbance of the signal when the ambient temperature is close to the patient's respiration. When the ambient temperature is changing rapidly, the difference between the signals coming in on first and second signal lines 20 and 26 may lead to an erroneous conclusion as to the status of the patient's respiration parameters.

In order to alleviate this problem, Applicants have found that when the temperature within enclosure 14 or near the subject's breathing site and the ambient temperature are fairly close to each other, that the operations on the differences in the signals from the first temperature sensor 18 and second temperature sensor 24 should be adjusted to provide for a larger difference signal being operated upon. Thus, Applicant's respiration system 10 operates on a temperature set point ($T_{sp}$), which is calculated from either a lookup table or made as a function of the temperature found by first temperature sensor 18 and second temperature sensor 24 in a breathing cycle. In this manner, the signal difference between the signal coming into feedback error signal processor 98 and particularly temperature controller processor 22 and the signal coming into temperature controller 22 from second temperature sensor 24 on line 26 is based upon the temperature of first temperature sensor 18 and the temperature set point.

As has been previously indicated, both first and second temperature sensors 18 and 24 may be thermistors, however, other types of sensors are commercially available and may be used in the practice of the subject system 10. First temperature sensor 18 is positioned for measuring the temperature of the breath or respiration ($T_m$) of patient 12. First temperature sensor 18 is positionally located within enclosure 14 or near the subject's breathing site with the second temperature sensor 24 being positionally located in an external location for measuring the external ambient temperature ($T_a$) of the patient's surroundings. System 10 is configured to find a thermal balance between thermoelectric generator 16 and the preset temperature $T_{sp}$. The preset temperature is the variable set point which may be adjusted to maintain the surface temperature of the thermoelectric generator 16 at a temperature somewhat in the vicinity of the external ambient environment, but offset therefrom to provide a sufficient difference in the $|T_m-T_{sp}|$ which will yield a voltage signal from feedback error signal processor 98 of sufficient value to be clearly operable on.

Thermal balance is achieved through a feedback loop within feedback loop block 60 shown in FIGS. 2 and 3 where temperature being sensed by thermoelectric generator 16 is transmitted to temperature controller processor 22 and then to feedback signal processor 30, through power controller 34 and then back to thermoelectric generator 16. In this manner, the sensing and measurement of the surface temperature of thermoelectric generator 16 is continuously influenced by the temperature of the breath and is monitored with respect to the temperature set point where the thermoelectric generator 16 is continuously driven to the temperature set point calculated.

In overall concept, feedback error signal processor 98 is coupled to compensating power controller 100 and thermoelectric generator 16 in a feedback loop for inducing either cooling or heating. The feedback loop may be set up as an analog proportional controller or a proportional integrated derivative controller (PID) dependent upon specific environmental requirements.

The temperature values used to derive the breathing parameters or respiration of patient 12 are closely related to the preset temperature ($T_{sp}$), which is a value calculated and generally slightly offset from the ambient temperature ($T_a$) in the vicinity of the temperature monitoring device 10. As the ambient temperature in the vicinity of the thermoelectric generator 16 changes, the value of the preset temperature ($T_{sp}$) may be adjusted. However, in some cases where the ambient temperature ($T_a$) is expected to be substantially different than the breathing gas temperature, the value of a preset temperature ($T_{sp}$) is derived from measurements of the second temperature sensor 24.

Thermoelectric generator 16 is coupled to first temperature sensor 18 for generating the first voltage signal on first voltage signal line 20 dependent on the preset temperature ($T_{sp}$) during predetermined cycles of the patient's breathing. The patient's breathing cycles are determined by the inhalation and exhalation of the patient's breath. Thermoelectric generator 16 is configured to be continuously driven to the preset temperature ($T_{sp}$) during the patient's inhalation cycle. When the patient exhales, the patient breathes on the thermal sensor 18 and thermoelectric generator 16, and induces a difference in temperature across the thermoelectric generator 16 which is measured by the first temperature sensor 18.

In this manner, temperature controller processor 22 is programmed to determine a multiplicity of breathing gas temperatures of patient 12 over a predetermined time through use of the first signal on line 20 and the second signal passed on line 26 adjusted to the temperature set point. Temperature controller processor 22 may be programmed to analyze a multiplicity of breathing gas temperatures and may be programmed to determine a maximum breathing gas temperature during a cycle $T_m(t)_{max}$. Similarly, a minimum breathing gas temperature $T_m(t)_{mm}$ may be calculated. The time intervals may be the patient's cycle of inhalation/exhalation corresponding to a breathing period.

Where temperature controller processor 22 is used to provide a maximum and minimum breathing gas temperature during a breathing period, the processor 22 may calculate the difference between the maximum and minimum breathing temperatures and a threshold temperature $\Delta T_m$ where the threshold $\Delta T_m$ represents a difference below which a problem area may exist in the breathing cycle of patient 12.

In any event, temperature controller processor 22 generates an error voltage representative of the difference between the preset temperature $T_{sp}$ and the temperature measured by first temperature sensor 18 coupled to thermoelectric generator 16. Essentially temperature controller 22 may be a subtract circuit well known in the prior art for subtracting the temperature sensed by first temperature sensor 18 and the temperature set point which issues an intermediate feedback error signal on intermediate feedback error signal line 28 being transmitted by temperature controller processor 22.

The intermediate feedback error signal is a third signal that is output from temperature controller processor 22 on third output signal line 28 to be fed into feedback signal processor 30. Temperature controller processor 22 includes a processor memory which may include lookup tables with preset temperature values to provide temperature set points as a function of the ambient temperature. Ambient temperature value, as well as biasing temperature values or both values may be used as input criteria to identify a preset temperature value from the table based upon the input criteria used.

Where the first and second temperature sensors 18 and 24 are thermistors, the signal generated by first temperature sensor 18 will be a change in voltage or current across the thermistor due to the temperature-induced change in the resistance of the resistor contained in thermistor 18. The plurality of breathing gas temperatures may be determined over a period of time $T_m(t)$ so that the temperature at discrete points in time may be used to determine the maximum breathing gas temperature during some time interval as previously indicated.

Temperature controller processor 22 may be a proportional integral derivative controller (PID controller) which calculates an error value as the difference between a measured process variable and a desired set point. In the subject Application, a temperature set point may be obtained from a lookup table based upon the second ambient second temperature sensor 24 and temperature controller processor 22. A difference between the set point temperature and the temperature voltage signal from first thermal sensor 18 is calculated to produce intermediate feedback error signal or third signal output from temperature controller processor 22 on line 28 representative of the difference between the first input signal and the temperature set point.

The temperature difference or error signal between the first signal from first temperature sensor 18 and the preset temperature is fed to feedback signal processor 30 configured to perform error signal shaping through standard filtering and/or wave shaping for controlling an amount of error signal to be applied to compensating power controller 100 containing power controller 34. Feedback signal processor 30 permits specific operating parameters to be calculated for extracting a full temporal respiration signal without distortion. Such filtering circuits are well-known to those skilled in the art. An algorithm may be contained within feedback signal processor 30 for adapting its operation in a forward predicted manner based upon previously measured values.

Signals being transmitted to temperature controller processor 22 are generally analog in nature. Within temperature controller processor 22 there is an analog to digital converter (A/D) which provides for a digital signal to be transmitted on third or intermediate feedback error signal line 28 to feedback signal processor 30. By its nature the conversion from analog to digital signals results in spurious signals which are then smoothed and filtered in feedback signal processor 30.

Alternatively, the analog to digital converter may be within feedback signal processor 30 and analog signals on third line 28 are processed to digital signals within feedback signal processor 30. Subsequently, the signals in feedback signal processor 30 are smoothed and filtered and are transmitted to compensating power controller 100.

The breathing status of subject 12 is determined by comparing the variations in the magnitude of the error signal generated by temperature controller processor 22 that is smoothed and/or filtered in feedback signal processor 30 during any breathing cycle. Dependent upon the ambient temperature sensed by second temperature sensor 24, the preset temperature to which the subject's breathing is compared may be amended due to changes in the ambient temperature. Where there are changes in the ambient temperature, temperature controller processor 22, using an embedded logic or look-up reference table may compensate for such changes. The look-up table may be specific for a particular type of mask or enclosure 12 possibly being used, the age or size category of patient 12, or other information for properly assess the breathing status of the subject.

Feedback signal processor 30 is programmed to obtain information from the third signal passed on line 28 from temperature controller processor 22 and may be used to determine limits on normal respiration for a specific patient 12. In one aspect, the feedback signal processor 30 may be programmed to calculate the breathing rate and the tidal volume using the third signal output from temperature controller 22 on line 28.

The resulting smoothed and/or filtered signal generated within feedback signal processor 30 is then output as a fourth or processed electrical signal on fourth signal line 32 for input into power controller 34 of compensating power controller 100.

Power controller 34 may be a standard power controller that accepts the processed electrical signal generated by the components of feedback error signal processor 98. Power controller 34 is connected to a standard power source 102 where an electrical signal is inserted into power controller 34 on line 104. Power controller 34 generates a fifth or intermediate compensating signal on line 36 used for maintaining the preset temperature in the thermoelectric generator 16 during predetermined cycles of the patient's breathing.

The intermediate compensating signal is output from power controller 34 and passes on fifth signal input line 36 to inverter circuit 38 which is used for inverting the cycle of the signal generated by the first temperature sensor 18. As the patient breathes on thermoelectric generator 16, thermoelectric generator 16 generates heat which is measured by first temperature transistor 18. The first signal is passed on line 20 into temperature controller processor 22 in combination with the ambient temperature sensed by second temperature sensor 24. Within temperature controller processor 22, a set point temperature is calculated from lookup tables based on the temperature differential between the ambient temperature and temperature measured by first temperature sensor 18.

Responsive to a fourth signal input on line 32, power controller 34 will either generate current to heat or cool thermoelectric generator 16. A signal is output from inverter 38 on line 40 for either heating/cooling thermoelectric generator 16.

In this manner, a feedback loop is provided between thermoelectric generator 16, temperature controller processor 22, feedback signal processor 30, power controller 34, and inverter 38 to provide a continuous updating of the status of the patient's respiration.

Subsequent to the processed electrical signal being developed in feedback signal processor 30, the processed electrical signal may be inserted into respiration signal recovery processor 44 on line 42. Respiration signal recovery processor 44 is a wave shaping system for readable interpretation of the respiration status of patient 12. Respiration signal recovery processor 44 may include a shaping algorithm which is based on look-up tables that have been documented in many clinical studies. Respiration signal recovery processor 44 produces a set of respiration based waveforms which may be analyzed for comparing and calculating the patient's actual respiration status on some type of display 50 well-known in the art.

Output of the wave shaped packets provided in respiration signal recovery processor 44 are output on line 46 to display 50 which may include a digital to analog converter which allows a direct analog output and can be fed to a chart recorder, computer screen, or some similar readout device for display.

Display 50 may include an alarm, other audio or visual warning device where the patient's respiration status is published when determined to be below or above a predetermined value. Archival storage may be accomplished onboard respiration recovery processor 44 by using known available memory or storage devices.

Compensating power controller 100 contains both power controller 34 and inverter circuit 38 although in some instances it is envisioned that both power controller 34 and inverter 38 are part of a single module.

Inverter 38 may be a H-bridge device, which switches the polarity of the power input to thermoelectric generator 16 to effect heating or cooling. Inverter 38 may also be a bipolar operational amplifier with an output which swings through zero crossings without introducing noise which would be typical of a pulse width modulation (PWM) technique or physically switching the H-bridge polarity.

In the embodiment shown in FIG. 3, thermal mass 52 is mounted to thermoelectric generator 16 for transporting heat away from thermoelectric generator 16 during predetermined time intervals of a patient's respiration cycle. Thermal mass 52 may be formed of one or more types of thermally conductive compositions such as copper, aluminum, diamond, gold, and related compositions. In the preferred embodiment, the thermal mass 52 is contiguously mounted to thermoelectric generator 16 for providing a path of least resistance to heat being transported.

Thermal mass 52 may essentially be a precisely sized block or fin formed of a thermally conductive material and provides for a quick heat transport mechanism to permit a quick recovery of thermoelectric generator to the pre-set temperature during breathing cycles.

Figure 4:
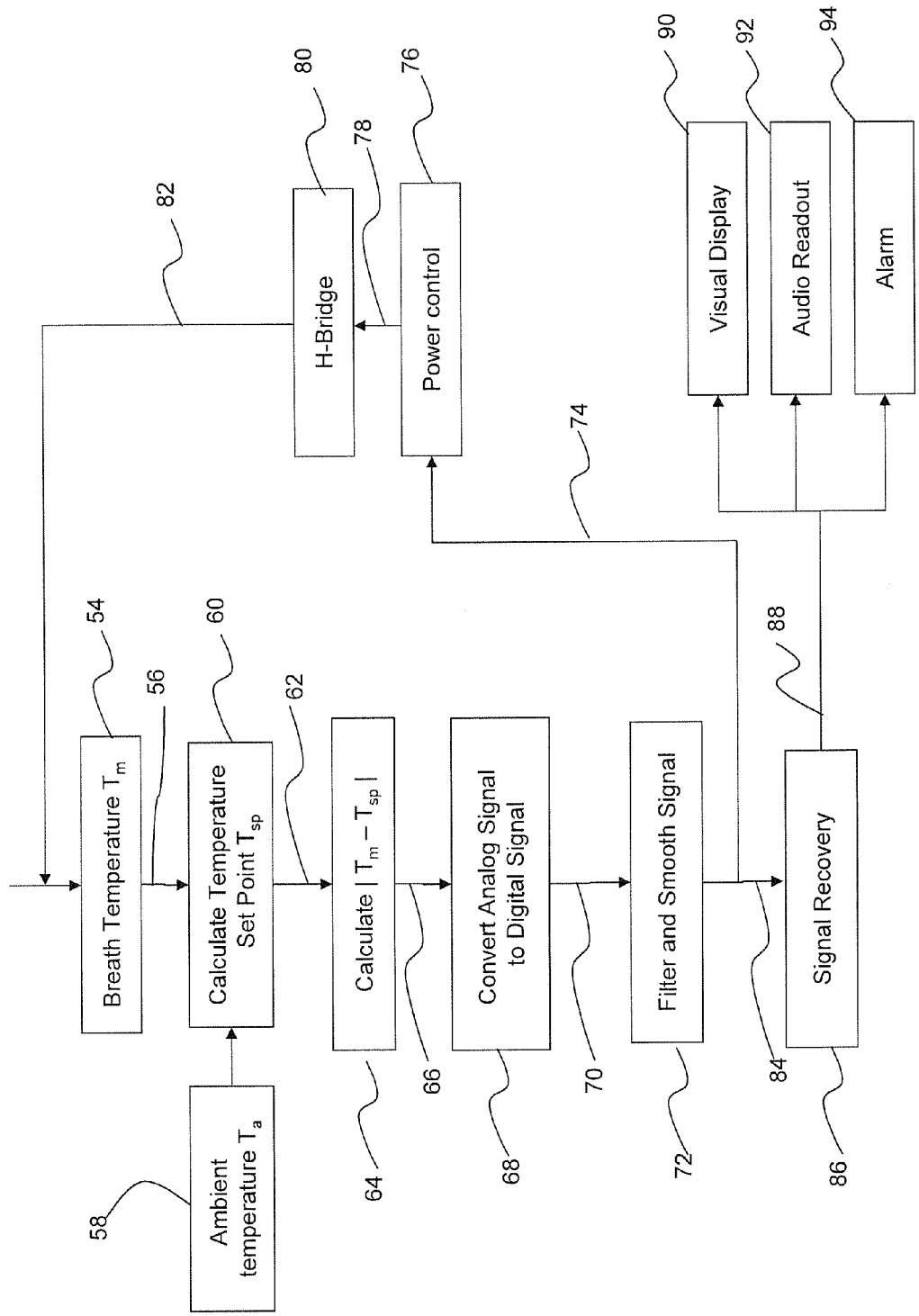

Referring now to FIG. 4, there is shown a method for monitoring the respiration of patient 12 within enclosure 14. The overall feedback looping process and method is initiated in block 54 where patient 12 breathes on thermoelectric generator 16. The first signal previously referred to is generated and issued by the first temperature sensor 18 and the logic flows on line 56 to block 60 where a temperature set point is calculated within feedback error signal processor 98, which is inserted into block 60 by second temperature sensor 24 in block 58. Second temperature sensor 24 measures the ambient external temperature of the environment. In block 60, temperature controller processor 22 within feedback error signal processor 98 calculates a temperature set point based upon the ambient temperature measured in block 58 and the patient's breath temperature in block 54. Information then passes on line 62 to block 64 where the temperature controller processor 22 calculates the difference in the breath temperature sensed in block 54 and the temperature set point calculated in block 60. The difference between the breath temperature and the set point temperature is passed on line 66 to block 68 where there is a conversion of the analog signal on line 66 to a digital signal.

Once the analog to digital signal representing the difference between the patient's breath temperature and the temperature set point is converted, the information passes on line 70 to block 72 which may be incorporated within feedback signal processor 30 for smoothing and filtering the digital signal. Alternatively, the conversion of the analog to digital signal represented in block 68 may be a portion of block 72 where the analog to digital signal is converted in feedback signal processor 30.

The smoothed and filtered signal, which passes on line 84, is representative of the fourth signal line 32 previously described. The information passes to power control block 76, which generates power based upon the difference in the signal exiting block 72. Power is inserted into H-bridge block 80 on line 78. It is to be understood that block 80 may be incorporated within power control block 76 as part of an overall system. In any event, the signal is then inserted on line 82 back to the thermoelectric generator 16 represented by block 54 in this FIG. 4.

In this manner, there is provided a method for monitoring the respiration of the patient 12 in a feedback loop system, which essentially provides for respiration parameters which are substantially independent of the external environment.

Returning back to the filtered and smoothed filtered signal in block 72, such is further inserted into signal recovery block 86 through line 84 for preparation of signal recovery which may be read. The signal emanating from signal recovery block 86 on line 88 is inserted into either visual display 90 which may be analogous to the display system 50. Additionally, the recovered signal from on line 88 may be similarly inserted into an audio readout display as represented by block 92 or in the event that necessary action must be taken, into an alarm block 94. It is to be understood that information blocks 90, 92, and 94 may all be incorporated into one standard display system 50, as was previously described in relation to FIGS. 1-3.

The calculations that are used to derive the breathing properties are closely related to the set point temperature $T_{sp}$, a value that is relatively close to the expected temperature of the vicinity of the thermoelectric generator's 16 temperature but somewhat different from the expected exhaled breath temperature. As the ambient temperature in the vicinity of the thermoelectric generator 16 changes, the value of $T_{sp}$ will also have to be adjusted. In cases where the ambient temperature is expected to be much different than the exhaled breath temperature its value may be derived from measurements of a dedicated thermistor. $T_m(\tau)$ are values that are continuously obtained from the thermoelectric generator 16. These values are tabulated every predetermined time $\Delta t$ that is much shorter than an expected breathing cycle. Thus, $\tau=t/\Delta t$ where t is the time in seconds from the start of the monitoring operation. A typical value of $\Delta t$ would be 0.1 sec. The $T_m(\tau)$ values are stored in an array called $T_m$. To correct for any possible "noise" in the data stream a simple smoothing algorithm can be employed, such as the so-called Box-Car algorithm, where the value of each reading is averaged with n previous and n subsequent values, where "n" is a small number, typically 1-5. The corrected array is called $T_{mc}(\tau)$ $$T_{mc}(\tau) = \frac{1}{2n+1} \sum_{\tau-n}^{\tau+n} T_m(\tau) \tag{1}$$

Since the values of the $T_{mc}$ depend on the n earlier and the n later values of $T_m$, it is filled at the same rate as the $T_m$, array but delayed by the time it takes to acquire n+1 values. The maximum values $MaxT_{mc}(\tau)$ and the minimum values $MinT_{mc}(\tau)$ within a breathing cycle are derived by an algorithm that searches for maximum and minimum values respectively within an "m" previous and consecutive values of $T_{mc}(T)$, where "m" is typically on the order of 5-10.

Since the values of $MaxT_{mc}(\tau)$ and $Min\ T_{mc}(\tau)$ depend on the "m" earlier and the "m" later values of $T_{mc}(\tau)$ they are derived at the rate that the $T_{mc}$ array is filled but with a delayed of m+1 values.

The values of $MaxT_{mc}(\tau)$ are stored in a $MaxT_{mc}(2,j)$ matrix where j=1,k and k is a very large number. The derived $MaxT_{mc}(\tau)$ values are stored in the $MaxT_{mc}(1,j)$ locations and the corresponding $\tau$ in the $MaxT_{mc}(2,j)$ locations. Similarly the values of $MinT_{mc}(\tau)$ are being stored in a $MinT_{mc}(2,j)$ matrix where j=1,k and k is a very large number. The derived $MinT_{mc}(\tau)$ values are stored in the $MaxT_{mc}(1,j)$ locations and the corresponding $\tau$ values in the $MaxT_{mc}(2,j)$ locations.

Using the values of $MaxT_{mc}$ and $MinT_{mc}$ the breathing rate, which corresponds to the number of maximum or minimum values per minute, are derived.

The difference between consecutive $MaxT_{mc}(1,j)$ and $MinT_{mc}(1,j)$ when averaged over a small number of cycles, provide an indication on the breathing condition of the subject as well as an estimate the tidal volume (size of breath). In a system with a data display capabilities, the arrays $T_{mc}$, $MaxT_{mc}$, and $MinT_{mc}$ can be displayed on display 50.

In certain embodiments, instead of a lookup table, FPGA based devices may be programmed to operate in several modes. The modes will be designed to indicate levels of breathing that are considered satisfactory for particular groups of patients. If the operator (physician, nurse or technician) deems the patient's breathing patterns to be satisfactory, he/she will select the desired operating mode and instruct the device to use those data as the base line. On the other hand, if the operator (physician, nurse or technician) deems the patient's breathing patterns to be unsatisfactory, he/she will select the desired operating mode based on stored data for the patient's age and weight and the breathing apparatus. (The selection of desired operating mode can be done by a push button.) A deviation from the baseline by a predetermined amount would sound an alarm.

In such a device, the microprocessor may be programmed to compare the threshold value for $T_{mc}(\tau)$ obtained from the reference table with the current calculated value for $T_{mc}(\tau)$. If the threshold value exceeds the calculated value, the audible alarm may be activated in order to alert medical personnel of a problem. In addition, the difference between the threshold value and the calculated value may be used by the microprocessor to determine which combination of the LEDs should be illuminated.

The invention can be used to create a device, which is low cost, portable, continuous and reliable. Further, the invention can be implemented as a lightweight device. Also, a small handheld device according to the invention can operate using an internal battery, as well as an approved wall power adapter.

This feature allows for temporary transport and operation, as well as extended operation of the unit when necessary. In addition, a memory device can be included which will extract and store information about the patient's breathing. Later, the information in the memory can be accessed, downloaded and analyzed.

In addition, this device can be equipped to transmit the acquired respiratory data to a data processing computer that provides additional enhanced capabilities to medical personnel. The data processing computer can store the data for later analysis, provide long term trend graphs of the raw and processed data, and assist in both long term studies as well as real time monitoring using powerful visual displays such as graphs, charts and LED's.

It will now be recognized that a device according to the invention can be a powerful tool for detecting apnea and hypoxia.

Although this invention has been described in connection with specific forms and embodiments thereof, it will be appreciated that various modifications other than those discussed above may be resorted to without departing from the spirit or scope of the invention as defined in the appended claims. For example, functionally equivalent elements or processes may be substituted for those specifically shown and described, certain features may be used independently of other features, and in certain cases, particular locations of the elements or processes may be reversed or interposed, all without departing from the spirit or scope of the invention as defined in the appended claims.

What is claimed is:

1. A respiration monitoring system for monitoring respiration parameters of a subject, comprising:
   (a) a first temperature sensor;
   (b) a thermoelectric generator thermally coupled to said first temperature sensor for generating an electrical signal of the subject respiration that depends on a preset temperature of said thermoelectric generator and the temperature of the subject's respiration, said thermoelectric generator to be driven to a calculated preset temperature;
   (c) a second temperature sensor to measure an ambient temperature;
   (d) a feedback error signal processor coupled to said thermoelectric generator and configured to develop and output a processed electrical signal that depends on said ambient temperature, said calculated preset temperature and said subject's respiration temperature; and
   (e) a compensating power controller electrically coupled to said feedback error signal processor and said thermoelectric generator for developing a compensating electrical signal input to said thermoelectric generator to drive said thermoelectric generator to said calculated preset temperature.

2. The respiration monitoring system as recited in claim 1, wherein said feedback error signal processor includes a temperature controller processor configured to (1) develop said calculated preset temperature dependent on said ambient temperature and said subject's respiration temperature, and (2) calculate a difference between said calculated preset temperature and said first sensor temperature.

3. The respiration monitoring system as recited in claim 2, wherein said feedback error signal processor includes a feedback signal processor configured to filter and smooth a transmitted temperature controller processor signal and generate said processed electrical signal.

4. The respiration monitoring system as recited in claim 1, wherein said processed electrical signal is representative of the difference between said calculated preset temperature and said subject's respiration temperature.

5. The respiration monitoring system as recited in claim 4, wherein said feedback error signal processor includes a feedback signal processor configured to filter and smooth a signal developed within said feedback error signal processor defining the difference between said calculated preset temperature and said subject's respiration temperature.

6. The respiration monitoring system as recited in claim 1, wherein said compensating power controller includes a power controller coupled to a power source and said feedback error signal processor for developing said compensating electrical signal responsive to said processed electrical signal transmitted from said feedback error signal processor.

7. The respiration monitoring system as recited in claim 6, wherein said power controller includes an inverter circuit for inverting a power controller signal during predetermined time intervals of a subject's breathing cycle and transmitting said inverted power control signal to said thermoelectric generator.

8. The respiration monitoring system as recited in claim 1, wherein said compensating power controller includes:
   (a) a power controller coupled to a power input and said feedback error signal processor for developing an intermediate compensating signal responsive to said processed electrical signal transmitted from said feedback error signal processor; and,
   (b) an inverter circuit coupled to said power controller and said thermoelectric generator, said inverter circuit for inverting said intermediate compensating signal and transmitting said inverted signal to said thermoelectric generator.

9. The respiration monitoring system as recited in claim 8, wherein said inverter circuit includes an H-bridge circuit.

10. The respiration monitoring system as recited in claim 1, wherein said thermoelectric generator, said feedback error signal processor, and compensating power controller are electrically coupled to form an electrical feedback loop for driving said thermoelectric generator to said calculated preset temperature.

11. The respiration monitoring system as recited in claim 1 including a thermal mass coupled to said thermoelectric generator for transporting heat from said thermal generator during predetermined times during a subject's breathing cycle.

12. The respiration monitoring system as recited in claim 11, wherein said thermal mass is a block member fixedly coupled to said thermoelectric generator and composed of a high thermal conductivity material.

13. The respiration monitoring system as recited in claim 12, wherein said thermal mass has a composition selected from the group of copper, aluminum and diamond.

14. The respiration monitoring system as recited in claim 1 including a visual display electrically coupled to said feedback error signal processor for visually displaying said processed electrical signal.

15. The respiration monitoring system as recited in claim 1 including an audio display electrically coupled to said feedback error signal processor for providing an audio signal responsive to said processed electrical signal.

16. The respiration monitoring system as recited in claim 1 including a respiration signal recovery processor connected to said feedback error signal processor and configured to process said processed electrical signal for display of said processed electrical signal.

17. The respiration monitoring system as recited in claim 16, wherein said respiration signal recovery processor is electrically connected to a visual display for visually displaying said processed electrical signal.

18. The respiration monitoring system as recited in claim 16, wherein said respiration signal recovery processor is electrically coupled to an audio display providing an audio signal responsive to said processed electrical signal.

19. A method of monitoring respiration of a subject, including the steps of:
(a) measuring a subject's respiration temperature by a first temperature sensor coupled to a thermoelectric generator;
(b) measuring an ambient temperature by a second temperature sensor positioned to measure the ambient temperature;
(c) calculating a thermoelectric generator preset temperature within a feedback error signal processor;
(d) forming a processed electrical signal based upon said subject's respiration temperature and said thermoelectric preset temperature;
(e) developing a compensating electrical signal within a compensating power controller electrically coupled to said feedback error signal processor;
(f) applying said compensating electrical signal to said thermoelectric generator so as to drive said thermoelectric generator to said thermoelectric generator preset temperature; and,
(g) repeating steps (a) through (f) throughout a plurality of breathing cycles of said subject.

20. The method of monitoring respiration of a subject as recited in claim 19, wherein the step of calculating said thermoelectric generator preset temperature includes the step of establishing said thermoelectric generator preset temperature as a function of said subject's respiration temperature and said ambient temperature.

21. The method of monitoring respiration of a subject as recited in claim 20, wherein the step of establishing said thermoelectric generator preset temperature includes the step of correlating said subject's respiration temperature with said ambient temperature on a look-up table within a feedback error signal processor coupled to said thermoelectric generator.

22. The method of monitoring respiration of a subject as recited in claim 20, wherein the step of establishing said thermoelectric generator preset temperature is followed by the step of subtracting said subject's respiration temperature from said thermoelectric generator preset temperature within said feedback error signal processor to form said processed electrical signal.

23. The method of monitoring respiration of a subject as recited in claim 19, wherein the step of forming said processed electrical signal includes the step of generating an intermediate feedback error signal calculated by subtracting said subject's respiration temperature from said thermoelectric generator preset temperature within a temperature controller.

24. The method of monitoring respiration of a subject as recited in claim 23, wherein the step generating said intermediate feedback error signal is followed by the step of smoothing said intermediate feedback error signal in a feedback signal processor.

25. The method of monitoring respiration of a subject as recited in claim 19, wherein the step of developing said compensating signal includes the step of transmitting said processed electrical signal to said compensating power controller connected to said feedback error signal processor and a power source for developing an intermediate compensating signal.

26. The method of monitoring respiration of a subject as recited in claim 25, wherein the step of developing said intermediate compensating signal is followed by the step of inverting said intermediate compensating signal at predetermined times within a subject's breathing cycle.

27. The method of monitoring respiration of a subject as recited in claim 26, wherein the step of inverting said intermediate compensation signal includes the step of coupling an H-circuit to a power controller within said compensating power controller.

28. The method of monitoring respiration of a subject as recited in claim 19, wherein the step of forming said processed electrical signal is followed by the step of processing said processed electrical signal to form a signal adapted to be visually sensed.

29. The method of monitoring respiration of a subject as recited in claim 19 including the step of attaching a thermally conducting member to said thermoelectric generator.

30. The method of monitoring respiration of a subject as recited in claim 19 including the step of displaying said processed electrical signal.

* * * * *